(12) United States Patent
Wakumoto et al.

(10) Patent No.: US 6,511,441 B1
(45) Date of Patent: Jan. 28, 2003

(54) SYSTEM FOR MEASURING TONGUE PRESSURE

(75) Inventors: Masahiko Wakumoto, Tokyo (JP); Shinobu Masaki, Kyoto (JP); Toshikazu Ooue, Nara (JP)

(73) Assignee: Advanced Telecommunications Research Institute International, Kyoto (JP)

( * ) Notice: Subject to any disclaimer, the term of this patent is extended or adjusted under 35 U.S.C. 154(b) by 0 days.

(21) Appl. No.: 09/763,341
(22) PCT Filed: Aug. 19, 1998
(86) PCT No.: PCT/JP98/03669
§ 371 (c)(1), (2), (4) Date: Jun. 15, 2001
(87) PCT Pub. No.: WO00/10450
PCT Pub. Date: Mar. 2, 2000

(51) Int. Cl.$^7$ .............................................. A61B 5/103
(52) U.S. Cl. ...................................... 600/590; 600/561
(58) Field of Search ................................. 600/590, 561, 600/373, 386, 393, 534, 535, 546

(56) References Cited

U.S. PATENT DOCUMENTS

| | | | | | |
|---|---|---|---|---|---|
| 3,524,932 A | * | 8/1970 | Stucki | .......................... | 600/590 |
| 3,983,865 A | * | 10/1976 | Shepard | ....................... | 600/590 |
| 4,112,596 A | * | 9/1978 | Fletcher et al. | ............. | 600/590 |
| 4,287,895 A | * | 9/1981 | Hori | ............................ | 600/595 |
| 4,334,542 A | * | 6/1982 | Takinishi et al. | ........... | 600/383 |
| 5,212,476 A | * | 5/1993 | Maloney | | |

FOREIGN PATENT DOCUMENTS

| | | | |
|---|---|---|---|
| JP | 55-122545 | * | 9/1980 |
| JP | 55-149970 | * | 11/1980 |

* cited by examiner

Primary Examiner—Stephen M. Hepperle
(74) Attorney, Agent, or Firm—Darby & Darby

(57) ABSTRACT

A system for measuring tongue pressure includes a thin palate floor plate, thin pressure sensor sheets, an attaching member and a cable. The shape of the thin palate floor plate matches with that of a palate. The thin pressure sensor sheets have a plurality of pressure sensing cells secured to the lower surface of the palate floor plate. The attaching member attaches the palate floor plate to a proper position in the palate. The cable transmits information from the pressure sensing cells of the pressure sensor sheets to an apparatus outside the palate, and is let out of the oral cavity extending around the back of the final gum tooth and passing along the vestibule of the oval cavity when the palate floor plate is attached in the palate. Each of the pressure sensor sheets has two resin backings structured in one body, each of which has a plurality of electrodes covered with a pressure-sensitive ink layer on one side. Between the backings, air is contained gastightly. The electrodes are opposed to each other via the pressure-sensitive ink. The portions corresponding to the opposing electrodes and the pressure-sensitive ink layer functions as the pressure sensing cells.

16 Claims, 10 Drawing Sheets

F I G . 1 0
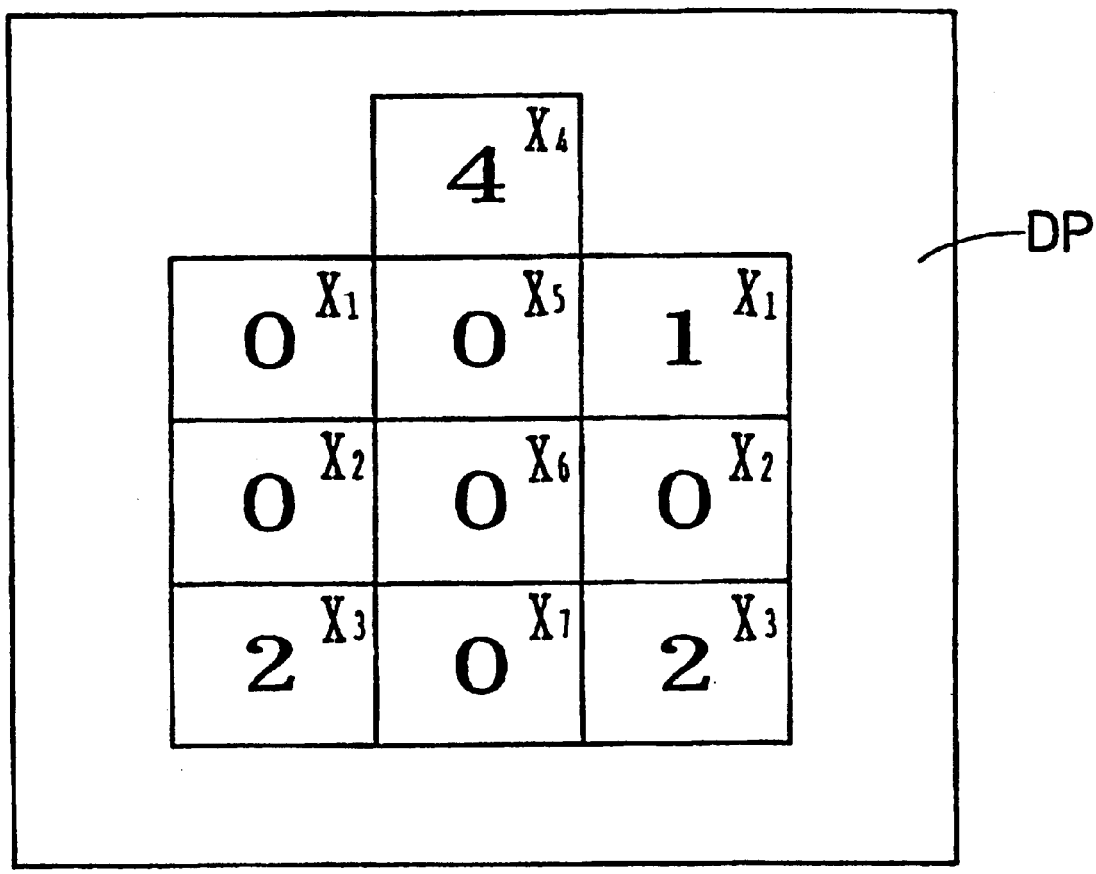

SYSTEM FOR MEASURING TONGUE PRESSURE

FIELD OF INVENTION

The present invention relates to a system for measuring contact pressure between a tongue and a palate during speech production (in this description, this system is referred to as a "tongue pressure measuring system"), and the system is applicable for the study of phonetic science, rehabilitation exercise for a person having articulation impediments, and so forth.

BACKGROUND ART

It is known that contact of a tongue with a palate is an important factor for pronouncing a consonant. Thus, an observation of contact condition of the tongue is very important for studying phonetic science and rehabilitation exercise for a person having articulation impediments.

Since the contact condition between the tongue and the palate at the time of utterance or during speech production cannot be observed directly, the following techniques (1) to (4) have been used. However, they have a variety of problems.

(1) Technique Using X-ray

This technique only enables the observation of an oral cavity from a single direction and cannot provide detailed information. This also has a problem of X-ray exposure.

(2) Technique Using MRI

This technique enables a three-dimensional observation of an oral cavity without the problem of X-ray exposure. However, because it takes time to obtain images, this technique is not suitable for imaging the contact conditions during production of most consonants.

(3) Technique Using Electro-palatography

In this technique, many electrodes are arranged on the palate of a speaker, and, based on the contact/noncontact information of the tongue with the electrodes, the contacting area is observed. However, it is impossible to observe a distribution or a variation of contact pressures.

(4) Technique Using a Strain Gauge type Pressure Sensor

This has been developed to overcome the drawbacks of the above techniques (1) to (3). However, in this technique, the sensor per se has a large size and, since the sensor also responds to a variation of pressure in an oral cavity, it it difficult to observe the accurate tongue-palate contact pressure per se.

Consequently, in the field utilizing these kinds of techniques, there has been a desired demand to develop a tongue pressure measuring system which can provide an accurate, real-time measurement of the tongue-palate contact pressure during speech production without disturbing natural utterance.

SUMMARY OF THE INVENTION

It is hence an object of the present invention to provide a tongue pressure measuring system which can provide an accurate, real-time measurement of the tongue-palate contact pressure during speech production without disturbing natural utterance.

The tongue pressure measuring system according to the present invention includes a thin palate floor plate in a shape matching with the shape of a user's palate, thin pressure sensor sheets having a plurality of pressure sensing cells secured to a lower surface of the palate floor plate, an attaching means for attaching the palate floor plate to a proper position on the palate and cables for transmitting information from the respective pressure sensing cells of the pressure sensor sheets to an apparatus outside of an oral cavity. The cables are led out of the. oral cavity extending around.the rearmost tooth and passing along the vestibule of the oral cavity with the palate floor plate being attached on the palate. Each of the pressure sensor sheets includes two resin backings structured in one body and contains air therein hermetically along an outline thereof. The backings include a plurality of electrodes covered with pressure-sensitive ink layers on one side of each backing, and the electrodes are opposed to each other through the pressure-sensitive ink layers. Portions corresponding to the opposing electrodes and the pressure-sensing ink layers form the pressure sensing cells.

The tongue pressure measuring system according to the present invention includes a thin palate floor plate in a shape matching with the shape of a user's palate, thin pressure sensor sheets having a plurality of pressure sensing cells secured to a lower surface of the palate floor plate, an attaching means for attaching the palate floor plate to a proper position on the palate and cables for transmitting information from the respective pressure sensing cells of the pressure sensor sheets to an apparatus outside an oral cavity. The cable is led out of the oral cavity extending around the rearmost tooth and passing along the vestibule of the oral cavity with the palate floor plate being attached on the palate. Each of the pressure sensor sheets includes two resin backings structured in one body and contains air therein hermetically along an outline thereof. The backings have a plurality of electrodes on one side of each backing and the electrodes oppose to each other. The electrodes on one of the backings are provided with a pressure-sensitive ink layer. Portions corresponding to the opposing electrodes and the pressure-sensing ink layer form the pressure sensing cells.

In another embodiment of the tongue pressure measuring of the present invention, air is sealed within each of the pressure sensor sheets so as to form a gap between opposing pressure sensitive ink layers which coat the opposing electrodes.

In another embodiment of the tongue pressure measuring system of the present invention include air sealed within each of the pressure sensor sheets so as to form a gap between the electrodes and the pressure sensitive ink layer coated over the electrodes opposing thereto.

In another embodiment of the tongue pressure measuring system of the present invention air is allowed to flow around and back and forth among the pressure sensing cells.

In another embodiment of the tongue pressure measuring system of the present invention, each of the pressure sensor sheets has a least one air storage portion in communication with portion of the pressure sensing cells.

In a further embodiment of the tongue pressure measuring system of the present invention, the cables are coated with a non-conductive member.

The function of the tongue pressure measuring system of the present invention stated above will be described in detail in the following section of the detailed description of the preferred embodiments.

BRIEF DESCRIPTION OF THE DRAWINGS

FIG. 10 is a view showing a display on which tongue-palate contact pressure in response to an output from the tongue pressure input section of FIG. 1 is shown.

DETAILED DESCRIPTION OF THE PREFERRED EMBODIMENTS

The preferred embodiments of the present invention are described below in conjunction with the drawings.

Figure 1:
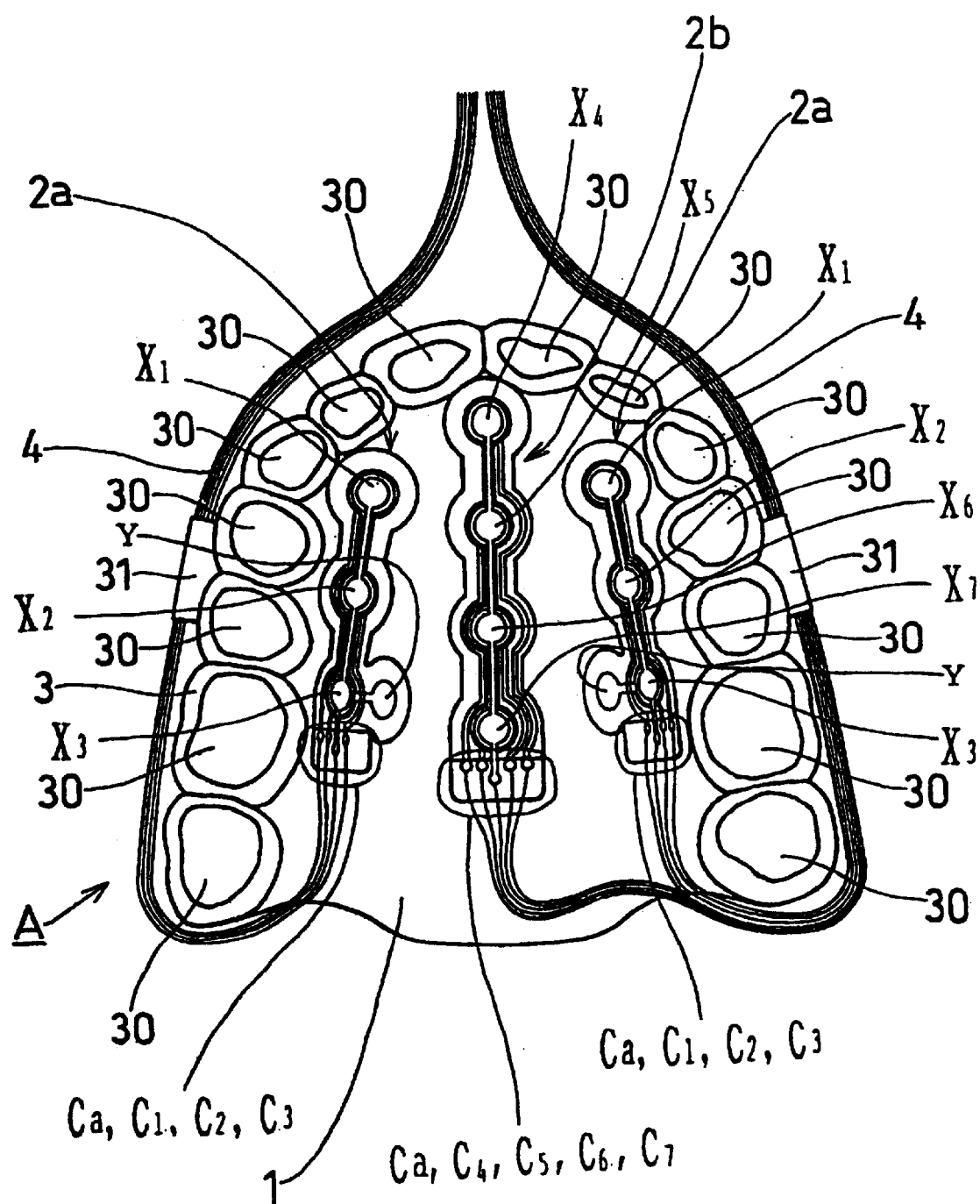
FIG. 1 is a view showing a tongue pressure input section of a tongue pressure measuring system of an embodiment of the present invention.
Figure 2:
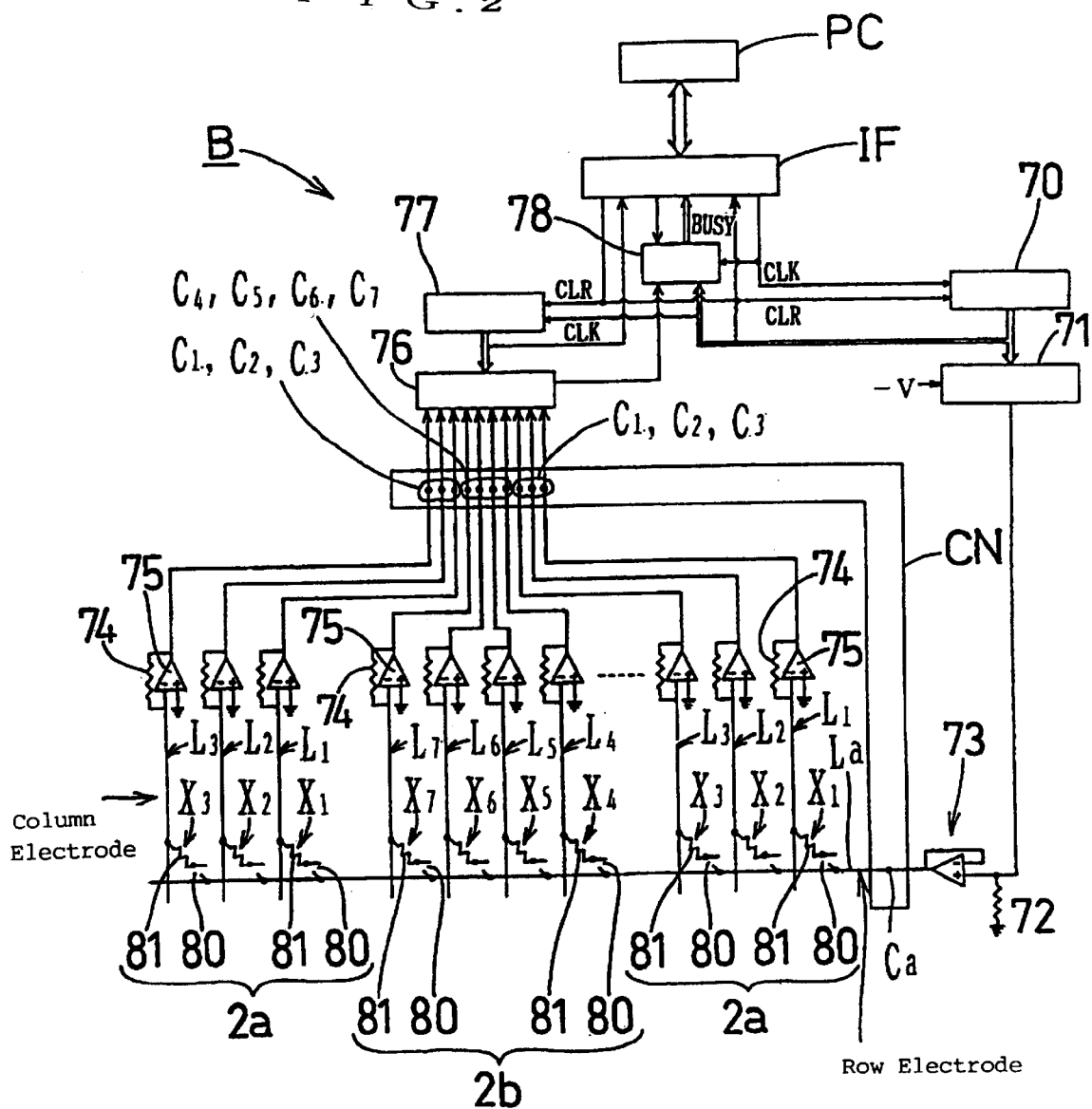
FIG. 2 is a diagram showing a circuit in the tongue pressure measuring system of an embodiment of the present invention, which allows a personal computer to read the output information from the tongue pressure input section of FIG. 1.

A tongue pressure measuring system of this embodiment is shown in FIGS. 1 and 2. The system includes a tongue pressure input section A to be attached to a palate of a speaker and an apparatus B which allows a personal computer to read output information from the tongue pressure input section A.

I) Structure of Tongue Pressure Input Section A

As shown in FIG. 1, the tongue pressure input section A includes a palate floor plate 1 in a shape matching with a shape of a palate of a speaker, thin pressure sensor sheets 2a, 2a and 2b respectively having a plurality of pressure sensing cells X secured to a lower surface of the palate floor plate 1, an attaching means 3 for attaching the palate floor plate 1 in a proper position of the palate, and cables 4 for transmitting output information from respective pressure sensing cells of the pressure sensor sheets 2a, 2b to the apparatus B disposed outside of an oral cavity.

(a) Palate Floor Plate 1

The palate floor plate 1 is made of thermoplastic resin and has an average thickness of about 0.5–1 mm. This palate floor plate 1 can be made of material other than thermoplastic resin as long as the material can be formed accurately matching with a shape of a palate of a speaker.

(b) Pressure Sensor Sheets 2a, 2b

Figure 3:
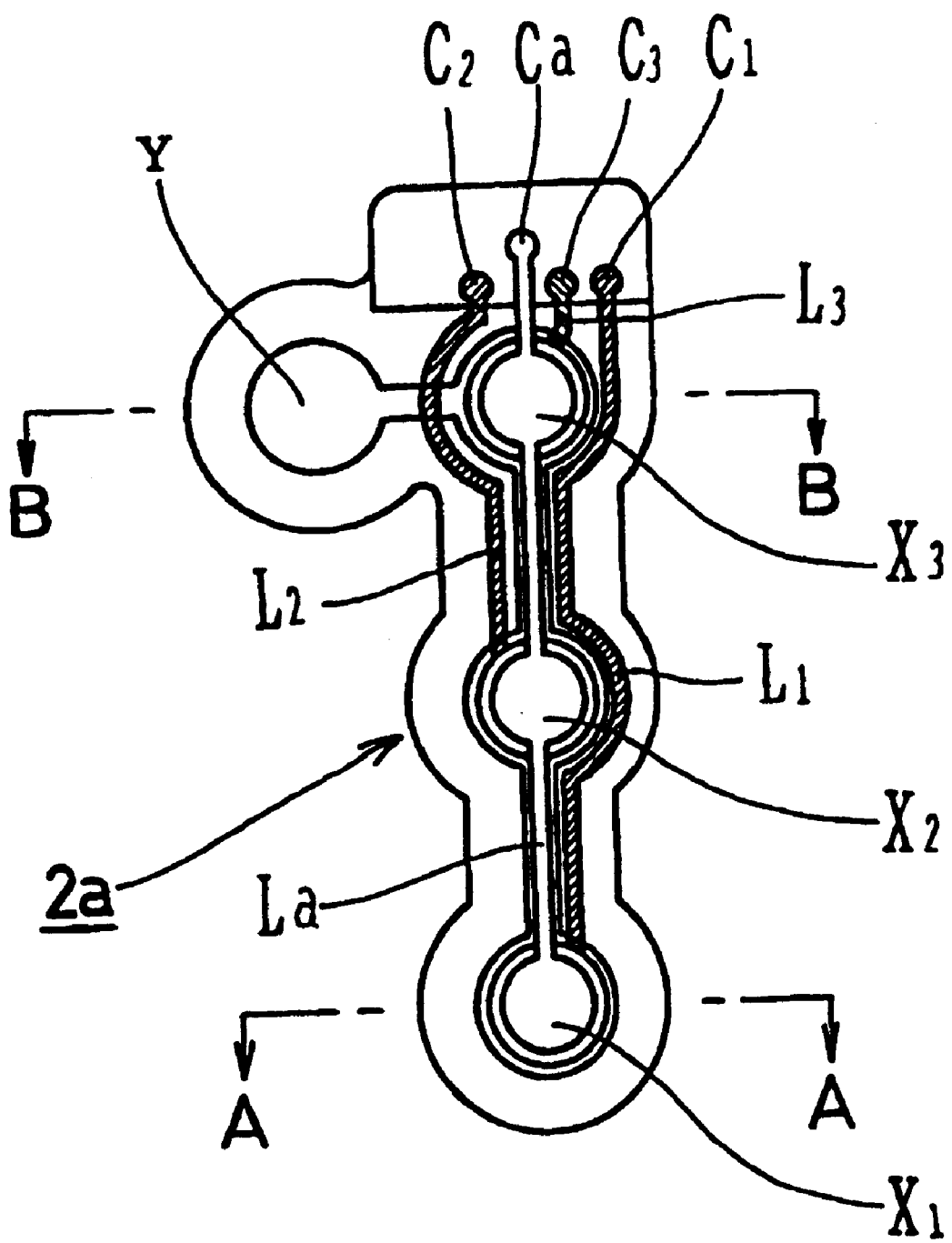
FIG. 3 is a plan view of a pressure sensor sheet used in the tongue pressure input section of FIG. 1.

As shown in FIGS. 1 and 3, the pressure sensor sheet 2a has a film-like shape of 0.1 mm in thickness as a whole.

The sheet includes in its inside three pressure sensing cells $X_1$, $X_2$ and $X_3$ among which air can communicate and each of which has a diameter of about 3 mm, a single air storage portion Y which can have air communication with the pressure sensing cell $X_3$, and four terminals Ca, $C_1$, $C_2$ and $C_3$ which respectively connect to the pressure sensing cells $X_1$, $X_2$ and $X_3$ through conductive lines La, $L_1$, $L_2$ and $L_3$.

Figure 4:
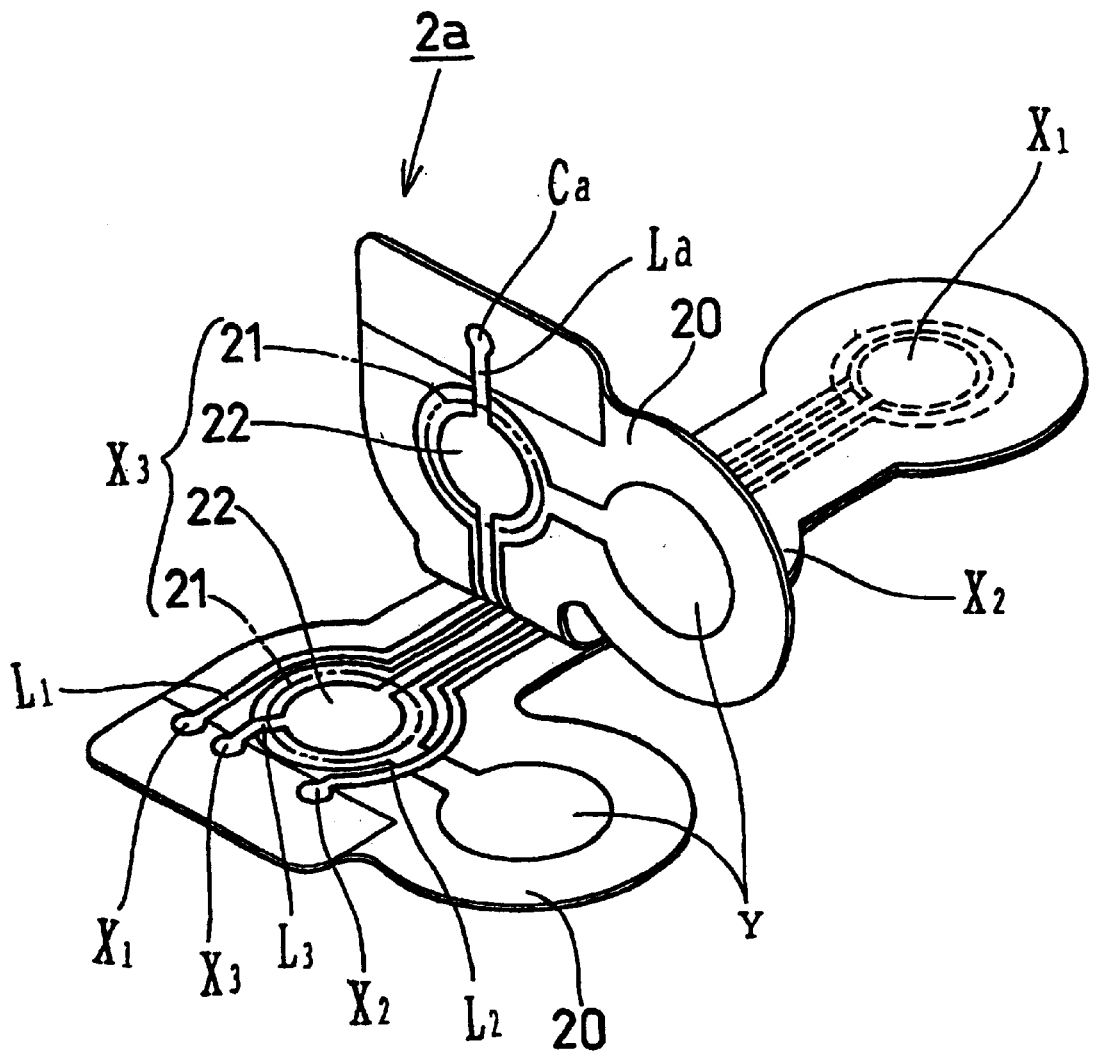
FIG. 4 is an exploded perspective view of the pressure sensor sheet of FIG. 3.
Figure 5:
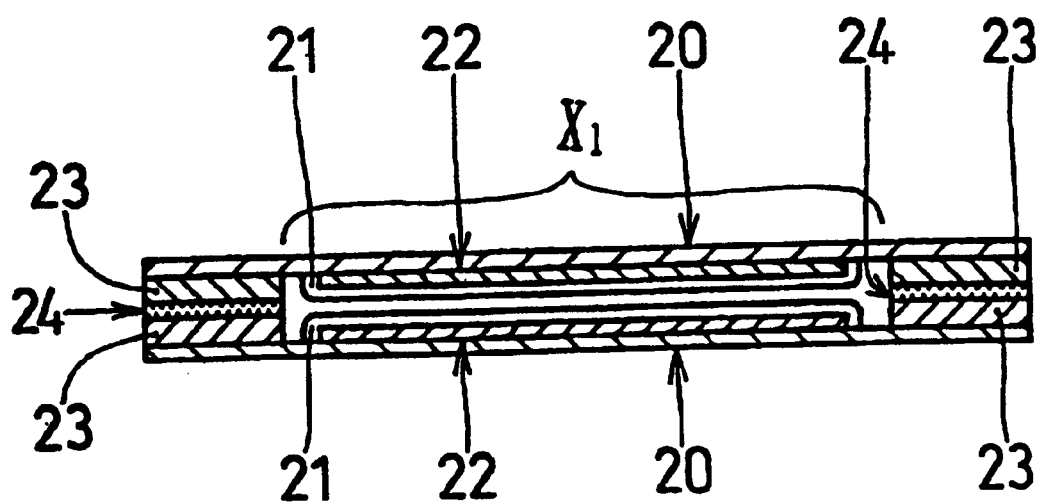
FIG. 5 is a sectional view taken along with the A—A line of the pressure sensor sheet shown in FIG. 3.
Figure 6:
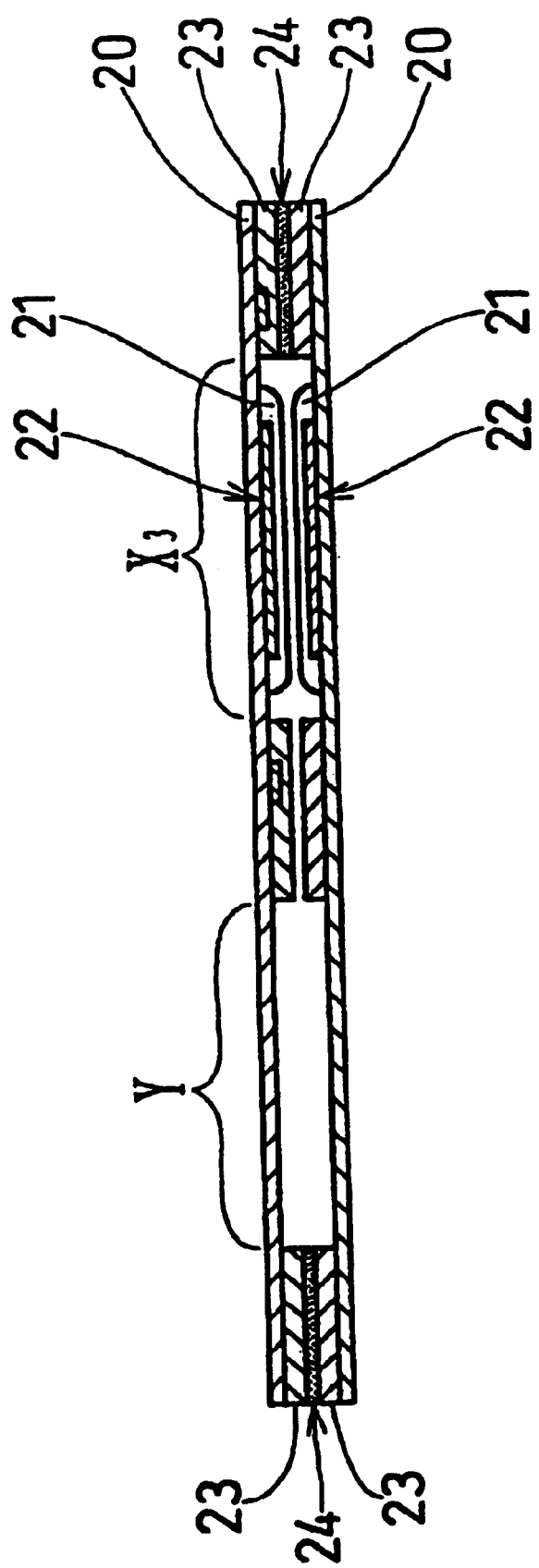
FIG. 6 is a sectional view taken along with the B—B line thereof.

As shown in FIG. 4, the pressure sensor sheet 2a is formed by unifying together two resin backings 20, 20, each of which has three electrodes 22 coated with a pressure sensitive ink layer 21 on one side, and setting the associate electrodes opposed to each other through the pressure sensitive ink layers 21, 21, and being sealed hermetically along the outline thereof and air is contained therein. It is preferable to have an amount of air to provide a very small gap between pressure sensitive ink layers 21, 21. The portions corresponding to the opposing electrodes 22, 22 and the pressure sensitive ink layers 21, 21 form the pressure sensing cells $X_1$, $X_2$ and $X_3$. The pressure sensing cells $X_1$, $X_2$, $X_3$ and the air storage portion Y are shown in FIGS. 5 and 6. They are insulated from outside by putting together insulating ink layers 23, 23 provided along the outlines of backings 20, 20 with a glue 24. And the electrodes 22, 22, the conductive lines La, $L_1$, $L_2$, $L_3$, and terminals Ca, $C_1$, $C_2$, $C_3$ are all formed by printing on the backings 20, 20 with conductive ink.

Figure 7:
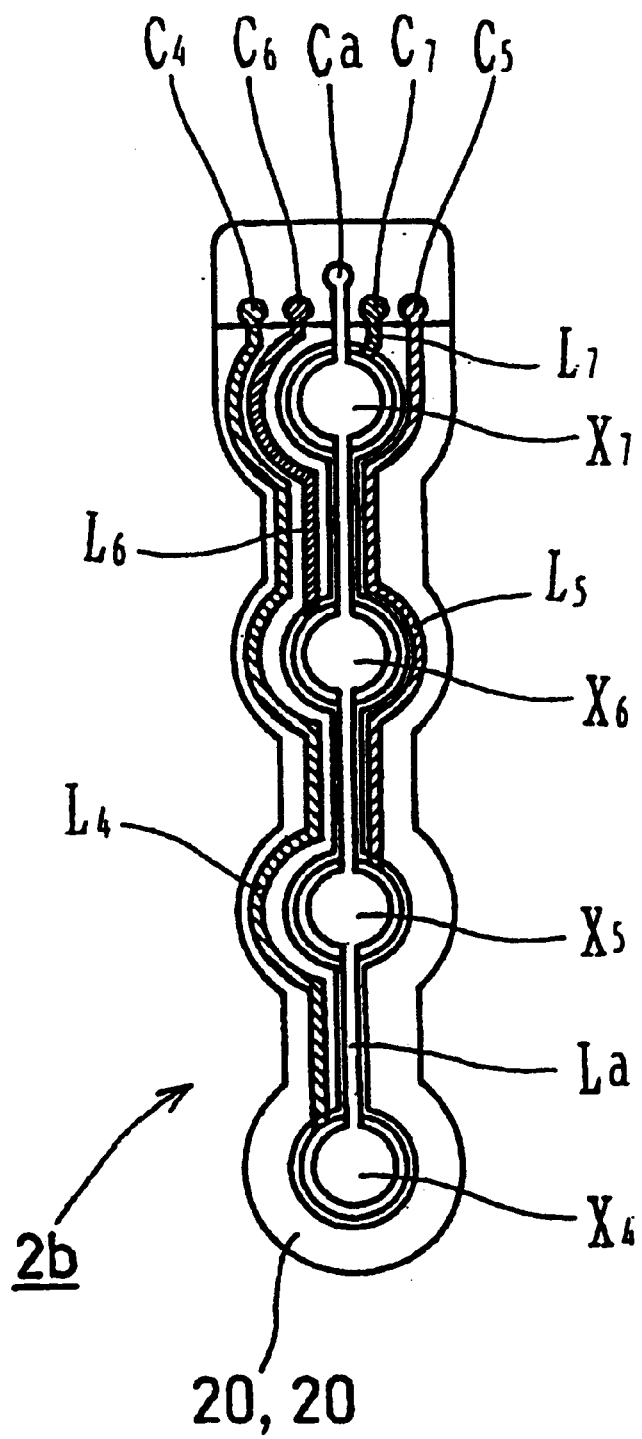
FIG. 7 is a plan view of another pressure sensor sheet.

As shown in FIG. 7, the pressure sensor sheet 2b has a film-like shape of 0.1 mm in thickness as a whole. The sheet 2b includes in its inside four pressure sensing cells $X_4$, $X_5$, $X_6$ and $X_7$ among which air can communicate, and four terminals Ca $C_4$, $C_5$, $C_6$ and $C_7$. These terminals are connected to the pressure sensing cells $X_4$, $X_5$, $X_6$ and $X_7$ through conductive lines La, $L_4$, $L_5$, $L_6$ and $L_7$. They are arranged substantially in the same manner as the pressure sensor sheets 2a described above.

In this embodiment, the conductive line La and the electrode 22 connected therewith correspond to a row electrode shown in FIG. 2 and the conductive lines ($L_1$, $L_2$, $L_3$), ($L_4$, $L_5$, $L_6$, $L_7$) and ($L_1$, $L_2$, $L_3$) and the electrodes 22 connected therewith correspond to a column electrode shown in FIG. 2.

Then, materials and dimensions of the pressure sensor sheets 2a and 2b are described in i–iv as follows:

i. Backings 20, 20
   Various kinds of flexible resin (such as, polyester resin) and the like; and
   thickness : 0.01–0.03 mm ii. Conductive ink forming electrodes 22, conductive lines lines La, $L_1$–$L_7$, and terminals Ca, $C_1$–$C_7$
   So-called Ag ink prepared by kneading silver powder in various kinds of resin (such as, polyester resin); and
   thickness of printed layer: 10–20 μm iii. Ink forming pressure sensitive ink layer 21
   Ink containing semiconductor and conductor particles in resin; and
   thickness of printed layer: 10–50 μm.

iv. Ink forming insulating ink layers 23, 23
   Ultraviolet setting resin; and
   thickness of printed layer: 5–30 μm.

(c) Attaching Means 3

Figure 8:
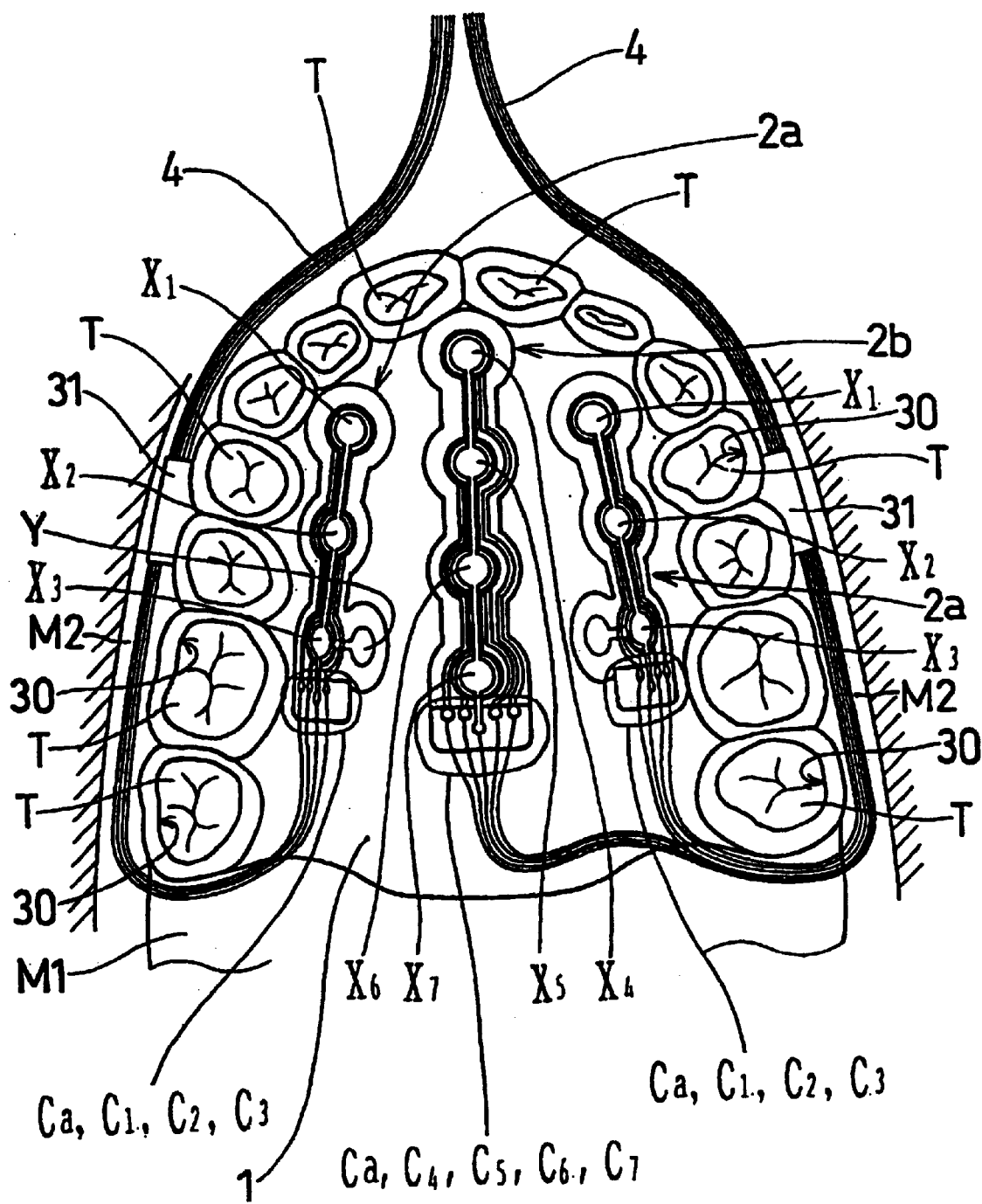
FIG. 8 is a view showing a state where the tongue pressure input section of FIG. 1 is attached on a palate.

As shown in FIG. 1, an attaching means 3 is made of the same material for the palate floor plate 1 as stated above and integrated with the palate floor plate 1. In particular, the means 3 includes tubular fitting portions 30 which open at upper and lower ends so as to be fixed to surround respective teeth T and are arranged along the outline of the palate floor plate 1 so as to correspond to a row of teeth. FIG. 8 shows the state that the palate floor plate 1 is attached on the palate Ml by means of the attaching means 3. Here, the cutting edges and palate surfaces of front teeth of an upper jaw and the occluding surfaces of molar teeth of the upper jaw are projected through the lower openings of the fitting portions 30 so that occlusion of the teeth can be normally performed. The outside surface of the attaching means 3 is integrally provided with supporting portions 31 for supporting cables 4.

(d) Cables 4

The cables 4, as shown in FIGS. 1 and 8, are provided in order to transmit output information from the respective pressure sensing cells $(X_1, X_2, X_3)$, $(X_4, X_5, X_6, X_7)$ and $(X_1, X_2, X_3)$ of the pressure sensor sheets 2a, 2a and 2b to the apparatus B located outside of the oral cavity. One ends of the cables 4 are electrically connected to terminals $C_a$, $(C_1, C_2, C_3)$, $(C_4, C_5, C_6, C_7)$ and $(C_1, C_2, C_3)$. The cables 4 are supported by the supporting portion 31 so as to be led out from the oral cavity extending along a route from an inner side of the rearmost molar tooth to the vestibule of the oral cavity, with the palate floor plate 1 being attached as shown in FIG. 8.

Therefore, with no intervention to the cables 4, occlusion of teeth can be performed.

The cables 4 have coating of non-conductive material on the outer surfaces.

II) Apparatus B to Allow a Personal Computer PC to Read Output Information from Tongue Pressure Input Section A As shown in FIG. 2, the apparatus B has a circuit for reading outputs from the pressure sensor sheet 2a, 2a and 2b, and is connected with a personal computer PC through an interface circuit IF. Operations of the computer PC, the interface circuit IF and the output reading circuit are known (disclosed in Japanese Patent Publication (Kouhyou) 62-502665), and not described in detail herein. On the other hand, a switch 80 and a resistor 81 shown in FIG. 2 represent schematically resistance of opposing portions of electrodes 22, 22 forming respective pressure sensing cells. When pressure is applied on pressure sensing cells $X_1-X_7$, the switch 80 turns to a closed state and resistance at a crossing point of row and column electrodes is switched from several mega ohms (high resistance) to an order of 1 kilo ohms (low resistance).

(1) At first, at the time of reading outputs from the pressure sensor sheets 2a, 2a and 2b, the foregoing reading circuit and the ends of the cables 4 are connected through a connector CN, as shown in FIG. 2.

(2) A voltage (−V) is applied to the row electrode through an amplifier 73 (an input side of the amplifier 73 is kept at the ground voltage by a resistor 72) in response to a clock signal "H" from the interface circuit IF.

(3) During an interval between an application of the voltage to the row electrode and a subsequent application thereof in response to a subsequent clock signal "H", a switch of a multiplexer 76 is turned in response to an output from a column counter 77 and the column electrodes are scanned sequentially.

(4) In this condition, when pressure is applied on the pressure sensing cells $(X_1, X_2, X_3)$, $(X_4, X_5, X_6, X_7)$ and $(X_1, X_2, X_3)$, the switch 80 turns to a close state and the resistance corresponding to the pressure changes to reduce and allows the current to flow to the column electrodes in sequence and to be invertedly amplified by resistors 74 and amplifiers 75 of respective columns. The invertedly amplified output voltage is sequentially transmitted to a register 78 by the multiplexer 76 and transferred to the interface circuit IF as a digital signal.

(5) In this embodiment, the information transmitted to the interface circuit IF is read by the personal computer PC and, as shown in FIG. 10, a display DP shows numerals (or colors) corresponding to the pressures applied on the pressure sensing cells $(X_1, X_2, X_3)$, $(X_4, X_5, X_6, X_7)$ and $(X_1, X_2, X_3)$.

III) Function of the Tongue Pressure Measuring System

With the tongue pressure measuring system according to the present invention, as described below, it is possible to accurately measure realtime tongue-palate contact pressure during speech production without being disturbed.

(a) No Disturbance of Natural Utterance

As stated above, the attaching means 3 includes tubular fitting portions 30 which open at upper and lower ends so as to be fixed to surround respective teeth T and are arranged along the outline of the palate floor plate 1 so as to correspond to a row of teeth. In the state the palate floor plate 1 is attached on the palate M1, the cutting edges and palate surfaces of front teeth of an upper jaw and the occluding surfaces of molar teeth of the upper jaw are projected through the lower openings of the fitting portions 30 so that occlusion of teeth can be normally performed. The shapes and/or arrangement of the fitting portions 30 can be preferably modified according to the row and occluding condition of the teeth of respective wearers.

The cables 4 are led out of the oral cavity extending around an inner side of the rearmost tooth, passing the vestibule of the oral cavity M2 in a state the palate floor plate 1 is attached on the palate M1. Thus occlusion of teeth can be performed without interfering with the cables 4.

Therefore, it is obvious that the tongue pressure measuring system according to the present invention does not disturb natural utterance.

(b) Accurate Measurement of the Tongue-palate Contact Pressure During Speech Production The plurality of pressure sensing cells formed on the pressure sensor sheets 2a, 2a and 2b are insulated from outside and sealed tight with a suitable amount of air being contained. Furthermore such air can communicate back and forth among the pressure sensing cells.

Therefore, if the pressure inside the oral cavity changes, air in the pressure sensing cells X is balanced among them and there will be no influence in output. On the other hand, tongue contact gives partial pressurization locally, not on the entire pressure sensor sheets, air present at a position corresponding to the portion with which the tongue contacts flows depending on the pressure difference.between the pressurized portion and the other pressure sensing cells X and the air storage portion Y without affecting the tongue contact pressure, and consequently the pressure sensing cells X respond only to the tongue pressure. Therefore, it is clearly understood that the present system using these pressure sensor sheets 2a, 2a and 2b can accurately measure the tongue-palate M1 contact pressure during speech production.

(c) Real-Time Measurement of Tongue-palate Contact Pressure During Speech Production It is clearly understood from the circuit structure and the function of the apparatus B stated above that the present system enables real-time measurement of the tongue-palate contact pressure during speech production.

IV) Other Embodiments

Figure 9:
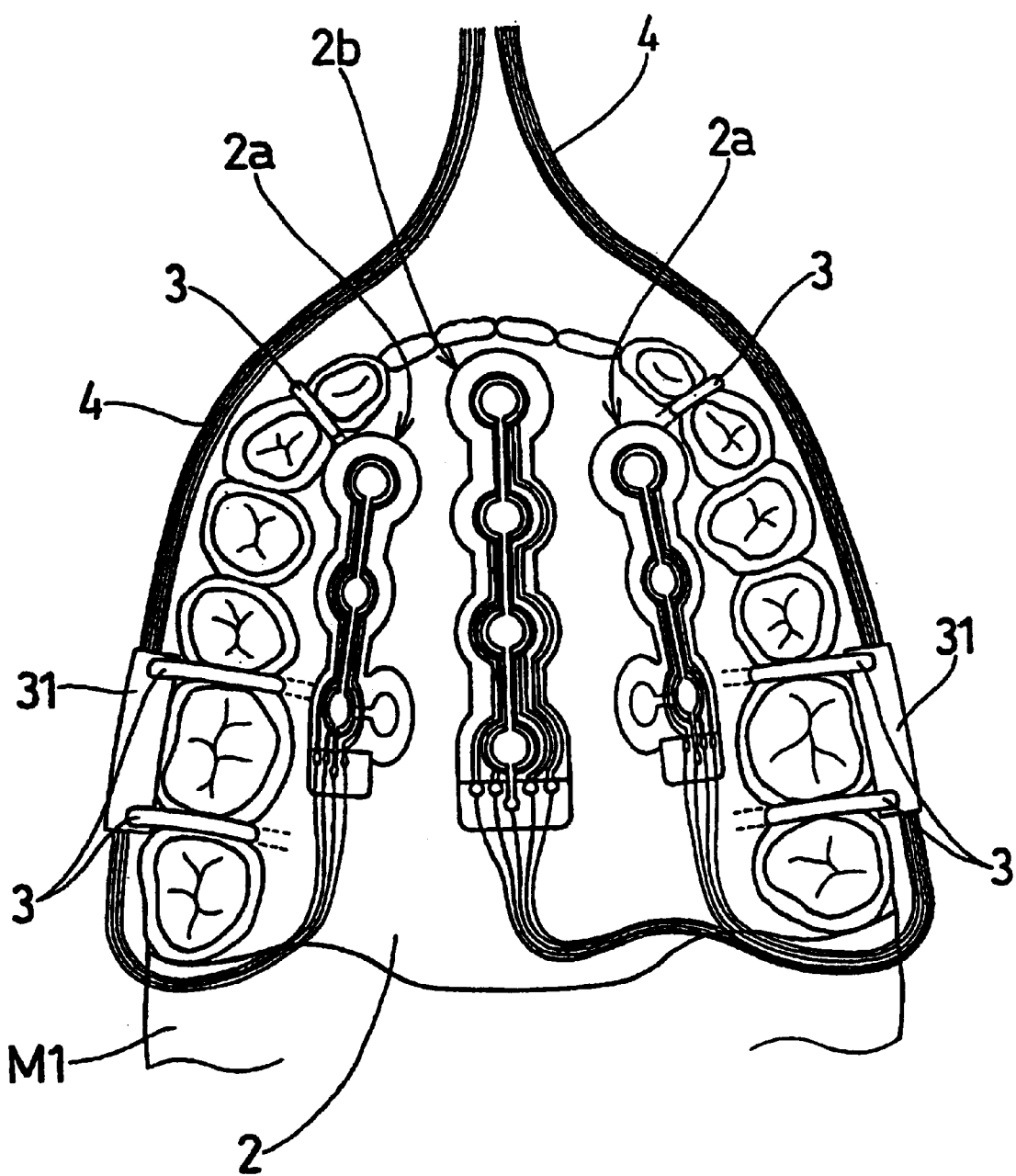
FIG. 9 is a view showing a tongue pressure input section of another embodiment.

Substituting for the attaching means 3 in the above embodiment, an attaching means 3 may include metal wires protruded from the palate floor plate 1 as shown in FIG. 9. These metal wires being inserted between teeth, the palate floor plate 1 may be attached on the palate M1. It is advisable that this type of attaching means 3 may have supporting means 31 making use of the metal wires constituting the attaching means 3. Positions and configurations of the metal wires may be modified suitably according to the row of teeth and the occlusion condition of wearers.

Moreover, the foregoing embodiments have three pressure sensor sheets 2a, 2a and 2b secured on the palate floor plate 1, but the number of pressure sensor sheets is not limitative to three and, depending on cases, one, two, four or more pressure sensor sheets may be used.

Furthermore, different from the above embodiments, all of the pressure sensor sheets 2a, 2a and 2b may respectively have air storage portions Y, and alternatively none of them may have such.

The number of the pressure sensing cells X on each pressure sensor sheet can be suitably changed.

In case that a pressure sensor sheet has many pressure sensing cells X different from the above embodiments, a plurality of row electrodes may be provided.

In this case, when the count of the row counter 70 increases by "1" in response to a clock signal from the interface circuit IF, the switch of the multiplexer 71 turns corresponding to the count of the row counter 70, and voltage (−V) is applied sequentially on the row electrodes through an amplifier 73 (see FIG. 2).

The pressure sensing cells of the foregoing embodiments include opposing electrodes coated by pressure sensitive ink, but it is not limitative thereto, and the pressure sensing cells may be constituted with electrodes coated by pressure sensitive ink and those with no such coating opposing each other.

V) Application of the Tongue Pressure Measuring System

In the foregoing embodiments, this system is applied for detecting tongue-palate contact pressure during speech production of a wearer, but this is not limitative thereto. It may be used to detect movement of a tongue or food when a liquid or solid object is swallowed. Or furthermore, to detect contacting condition of a tongue damaged by illness or accident.

Being constructed as stated above, the present invention can provide the tongue pressure measuring system which can accurately measure the realtime tongue-palate contact pressure during speech production without disturbing natural utterance.

What is claimed is:

1. A tongue pressure measuring system comprising:
   a thin palate floor plate in a shape matching with a shape of a palate;
   thin pressure sensor sheets having a plurality of pressure sensing cells secured to a lower surface of said palate floor plate;
   an attaching means for attaching the palate floor plate to a proper position on said palate;
   a cable for transmitting information from said pressure sensing cells of said pressure sensor sheets to an apparatus outside of an oral cavity;
   said cable being led out of said oral cavity extending around a rearmost tooth and passing along a vestibule of said oral cavity with said palate floor plate being attached on said palate;
   each of said pressure sensor sheets having two resin backings structured in one body and containing air therein hermetically along an outline thereof wherein said backings are provided with a plurality of electrodes covered with pressure-sensitive ink layers on one side of each backings, said plurality of electrodes being opposed each other through said pressure-sensitive ink layers; and
   portions corresponding to said opposing electrodes and said pressure-sensing ink layers forming said pressure sensing cells.

2. A tongue pressure measuring system comprising:
   a thin palate floor plate in a shape matching with a shape of a palate;
   thin pressure sensor sheets having a plurality of pressure sensing cells secured to a lower surface of said palate floor plate;
   an attaching means for attaching said palate floor plate to a proper position in said palate;
   a cable for transmitting information from said pressure sensing cells of said pressure sensor sheets to an apparatus outside an oral cavity, said cable being led out of said oral cavity extending around an innermost tooth and passing along a vestibule of said oral cavity with said palate floor plate being attached in said palate;
   each of said pressure sensor sheets having two resin backings structured in one body and containing air therein hermetically along an outline thereof wherein said backings are provided with a plurality of electrodes on one side of each backing, said electrodes being opposed each other, and those electrodes on one of said backings are provided with a pressure-sensitive ink layer; and
   portions corresponding to said opposing electrodes and said pressure-sensitive ink layer forming said pressure sensing cells.

3. The tongue pressure measuring system according to claim 1 wherein air is sealed in each of said pressure sensor sheets so as to form a gap between said pressure sensitive ink layers respectively coating said opposing electrodes.

4. The tongue pressure measuring system according to claim 2 wherein air is sealed in each of said pressure sensor sheets so as to form a gap between said electrodes and said pressure-sensitive ink layer coated over said electrodes opposing thereto.

5. The tongue pressure measuring system according to claim 7 wherein in each of said sensor sheets has at least one air storage portion in communication with portion of said pressure sensing cells.

6. The tongue pressure measuring system according to claim 5 wherein said cable is coated with a non-conductive member.

7. The tongue pressure measuring system according to claim 1 wherein air is allowed to flow among said pressure sensing cells.

8. The tongue pressure measuring system according to claim 2 wherein air is allowed to flow among said pressure sensing cells.

9. The tongue pressure measuring system according to claim 3 wherein air is allowed to flow among said pressure sensing cells.

10. The tongue pressure measuring system according to claim 4 wherein air is allowed to flow among said pressure sensing cells.

11. The tongue pressure measuring system according to claim 8 wherein in each of said sensor sheets has at least one air storage portion in communication with portion of said pressure sensing cells.

12. The tongue pressure measuring system according to claim 9 wherein in each of said sensor sheets has at least one air storage portion in communication with portion of said pressure sensing cells.

13. The tongue pressure measuring system according to claim 10 wherein in each of said sensor sheets has at least one air storage portion in communication with portion of said pressure sensing cells.

14. The tongue pressure measuring system according to claim 11 wherein said cable is coated with a non-conductive member.

15. The tongue pressure measuring system according to claim 12 wherein said cable is coated with a non-conductive member.

16. The tongue pressure measuring system according to claim 13 wherein said cable is coated with a non-conductive member.

* * * * *

UNITED STATES PATENT AND TRADEMARK OFFICE
CERTIFICATE OF CORRECTION

PATENT NO.   : 6,511,441 B1
DATED        : January 28, 2003
INVENTOR(S)  : Masahiko Wakumoto It is certified that error appears in the above-identified patent and that said Letters Patent is hereby corrected as shown below:

<u>Title page,</u>
Item [73], Assignee, add -- Nitta Corporation, Osaka (JP) --

Signed and Sealed this

Tenth Day of June, 2003

JAMES E. ROGAN
*Director of the United States Patent and Trademark Office*